US009512159B2

(12) United States Patent
Myers et al.

(10) Patent No.: US 9,512,159 B2
(45) Date of Patent: Dec. 6, 2016

(54) METHODS FOR THE PRODUCTION OF 3-O-DEACTIVATED-4'-MONOPHOSPHORYL LIPID A (3D-MLA)

(71) Applicant: CORIXA CORPORATION, Wilmington, DE (US)

(72) Inventors: Kent R. Myers, Hamilton, MT (US); D. Scott Snyder, Hamilton, MT (US)

(73) Assignee: CORIXA Corporation, Wilmington, DE (US)

( * ) Notice: Subject to any disclaimer, the term of this patent is extended or adjusted under 35 U.S.C. 154(b) by 0 days.

(21) Appl. No.: 14/271,431

(22) Filed: May 6, 2014

(65) Prior Publication Data

US 2014/0243513 A1    Aug. 28, 2014

Related U.S. Application Data

(63) Continuation of application No. 11/621,306, filed on Jan. 9, 2007, now abandoned, which is a continuation of application No. 10/099,313, filed on Mar. 14, 2002, now abandoned.

(60) Provisional application No. 60/280,089, filed on Mar. 30, 2001.

(51) Int. Cl.
*A61K 35/00* (2006.01)
*C07H 13/06* (2006.01)
*C12P 19/04* (2006.01)
*A61K 39/00* (2006.01)

(52) U.S. Cl.
CPC .............. *C07H 13/06* (2013.01); *C12P 19/04* (2013.01); *A61K 2039/55572* (2013.01)

(58) Field of Classification Search
CPC .................... C07H 13/06; A61K 2039/55572; C12P 19/04
See application file for complete search history.

(56) References Cited

U.S. PATENT DOCUMENTS

| | | | |
|---|---|---|---|
| 4,384,044 A | 5/1983 | Kim et al. | |
| 4,436,727 A | 3/1984 | Ribi | |
| 4,436,728 A | 3/1984 | Ribi et al. | |
| 4,612,304 A | 9/1986 | Fukushi | |
| 4,912,094 A | 3/1990 | Myers et al. | |
| 5,057,598 A | 10/1991 | Pollack et al. | |
| 5,326,857 A | 7/1994 | Yamamoto et al. | |
| 5,552,141 A | 9/1996 | Ribi | |
| 5,554,372 A | 9/1996 | Hunter | |
| 5,846,789 A * | 12/1998 | Bhadra et al. | 435/101 |
| 5,855,913 A | 1/1999 | Hanes et al. | |
| 5,985,309 A | 11/1999 | Edwards et al. | |

FOREIGN PATENT DOCUMENTS

| | | |
|---|---|---|
| GB | 2220211 A | 1/1990 |
| WO | 94/00153 | 1/1994 |
| WO | 9421292 | 9/1994 |
| WO | 95/17210 | 6/1995 |
| WO | 96/33739 | 10/1996 |
| WO | 98/43670 | 10/1998 |
| WO | 99/56776 | 11/1999 |
| WO | 00/78353 | 12/2000 |
| WO | 01/70756 | 9/2001 |
| WO | 02/078637 | 10/2002 |

OTHER PUBLICATIONS

Chatterjee et al. Can. J. Microbiol. (1976) 22: 1540-1548.*
Chen et al. J. Infect. Dis. (1973) 128 supplement: S43-S51.*
Galanos et al. Eur. J. Biochem. (1969) 9: 245-249.*
Helander et al. FEBS Lett. (1997) 409: 457-460.*
Morrison et al. J. Biol. Chem. (1975) 250(8): 2911-2919.*
Qureshi et al. Biol. Chem. (1983) 258(10): 12947-12951.*
Qureshi and Takayama, "The Bacteria: Molecular Basis of Bacterial Pathogenesis vol. XI", Chapter 15: Structure and Function of Lipid A; 1990, pp. 319-338, Academic Press.
Ulrich, et al., "Monophosphoryl Lipid A as an Adjuvant, Past Experiences and New Directions", Ribi ImmunoChem Research, VACCINE 1995, 495-524.
Galanos, et al., "Biological Activity of Synthetic Heptaacyl Lipid A Representing a component of *Salmonella* Minnesota R595 Lipid A", Eur J. Biochem, 1986, No. 160(1) pp. 55-59.
Brozek, et al., "Biosynthesis of Lipid A in *Escherichia Coli*", Biological Chemistry, 1990, No. 265 (26) pp. 15410-15417.
Bishop, et al., "Transfer of palmitate four phospholipids to lipid A in outer membranes of Gram-negative bacteria." EMBO J.; 2000; pp. 5071-5080; vol. 15.
Brandenburg, et al., "Phase Diagram of Deep Rough Mutant Lipopolysaccharide from *Salmonella* minnesota R595" J. Struct. Biol.; 1992; pp. 93-106; vol. 108.
Boeckler, et al., "Immunogenicity of new heterobifunctional cross-linking reagents used in the conjugation of synthetic peptides to liposomes." J. of Immunological Methods; May 1996; pp. 1-10; vol. 191(1).
Chatterjee, et al., Canadian Journal of Microbiology; 1976; pp. 1540-1548; vol. 22(10).
Chen, et al., "Heterogeneity and biological activity of endotoxic glycolipid" The Journal of Infectious Diseases; Jul. 1973; pp. S43-S51; vol. 128 (Suppl).
Darveau, et al., "Procedure for isolation of bacterial lipo poly saccharides from both smooth and rough pseudomonas-aeruginosa and *salmonella-typhimurium* strains" Journal of Bacteriology; Aug. 1983; pp. 831-838; vol. 155(2).
European Search Opinion dated May 22, 2012 for Application No. 11176340.5, European equivalent of present U.S. Appl. No. 11/621,306, filed Jan. 9, 2007 (3 pages).

(Continued)

*Primary Examiner* — Susan Hanley
(74) *Attorney, Agent, or Firm* — Joseph J. Schuller; Jason C. Fedon

(57) ABSTRACT

The invention relates to a method for extracting lipopolysaccharide (LPS) from rough trough mutant bacteria cells by extracting the cells with an aqueous aliphatic alcohol having from 1 to 4 carbon atoms at a temperature between 35 and 65 degrees C. to produce cells having a reduced phospholipid content. The resultant cells are then extracted with chloroform/methanol to yield LPS.

12 Claims, 1 Drawing Sheet

(56) References Cited

OTHER PUBLICATIONS

European Search Opinion dated Feb. 11, 2013 for Application No. 111763405, European equivalent of present U.S. Appl. No. 11/621,306, filed Jan. 9, 2007 (2 pages).
Galanos, et al., A new method for the extraction of R lipopolysaccharides' Eur. J. Biochem; 1969; pp. 245-249; vol. 9.
Iglewski, et al., The Bacteria, XI, pp. 319-338 (Quereshi et al., "Structure and Function of Lipid A"), Academic Press, Inc., San Diego, CA; 1990.
Johnson, et al., "3-0--desacyl monophosphoryl lipid A derivatives: synthesis and immunostimulant activities" Journal of Medicinal Chemistry; 1999; pp. 4640-4649; vol. 42.
Kropinksi, et al., "Extraction and Analysis of Lipopolysaccharides from Pseudomonas aeruginosa strain PAO, and three rough mutants" Can. J. Microbiol.; 1979; pp. 390-398; vol. 25.
Molecular Cloning: A Laboratory Manual, pp. 68-69, Cold Spring Harbor Laboratory, (Maniatis et al., eds.), (1982).
Morrison, et al., "Fractions of lipo poly saccharide from *Escherichia-coli* strain 0-111 B-4 prepared by 2 extraction procedures." Journal of Biological Chemistry; Apr. 1975; pp. 2911-2919; vol. 250(8).
Mosmann, et al., "TH1 and TH2 cells: Different patterns of lymphokine secretion lead to different functional properties," Ann. Rev. Immunol.; 1989; pp. 145-173; vol. 7.
Myers, et al., Ribi Immunochem Research, A Critical Determinant of Lipid A Endotoxic Activity, 1990; pp. 145-156.
Ng, A.K. et al., "Comparison of the Chemical Structure and Biological Activities of the glycolipids of *Salmonella* mennesotat R595 and *Salmonella* typhimurium SL 1102" Infection and Immunity; Oct. 1974; pp. 938-947; vol. 10 (4).
Nikado and Vaara, Molecular Basis of Bacterial Outer Membrane Permeability, Microbiological Reviews; Mar. 1985; pp. 1-32; vol. 49(1).
Nurminen, et al., "Methanol extracts LPS from deep rough bacteria," Biochemical and Biophysical Research Communications; 1996; pp. 441-444; vol. 219(2).
Office Action (Notice of Reasons for Rejection (translation)), Japanese Patent Application No. 2008-049418, Dec. 14, 2010, pp. 1-4, Japan.
Office Action (Communication Pursuant to Article 94(3) EPC, European Patent Application No. EP11176340.5, Feb. 11, 2013, pp. 1-2, Germany.
Qureshi, et al., "Complete structure of lipid A obtained from the lipopolysaccharides of the heptoseless mutant of *salmonella* typhimurium, "J. Biol. Chem.; 1983; pp. 12801-12803; vol. 258.
Qureshi, et al., "The Journal of Biological Chemistry, Monophosphoryl Lipid A Obtained from Lipopolysaccharides of *Salmonella* Minnesota R595" May 1985; pp. 5271-5278; vol. 260(9).
Qureshi, et al., "Complete Structural Determination of Lipopolysaccharide Obtained from Deep Rough Mutant of *Escherichia coli*." J. Biol. Chem; 1988; pp. 11971-11976; vol. 263(24).
Rietschel, et al., "Chemical structure and biologic activity of bacteiral and synthetic lipid A," Reviews of Infectious Diseases; 1987; pp. S527-S536; vol. 9(Suppl. 5).
Sasaki, et al., "Monophosphoryl lipid A enhances both humoral and cell-mediated immune responses to DNA vaccination against human immunodeficiency virus type 1," Infect, Immun.; Sep. 1997; pp. 3520-3528; vol. 65(9).
Schlecht and Fromme, Zentralbl Bakteriola, Growth of *salmonella* r-mutants in submersed cultures. 2. Influence of growth phases on the lipopolysaccharide content of the bacteria and on the chemical composition and serological behaviour of the lipopolysaccharids 1980; German; pp. 352-353; vol. 248(3).
Schlecht and Fromme, Zentralbl Bakteriola, Growth of *salmonella* r-mutants in submersed cultures. 2. Influence of growth phases on the lipopolysaccharide content of the bacteria and on the chemical composition and serological behaviour of the lipopolysaccharids 1980; English Translation; pp. 352-365; vol. 248(3).
Takayama, et al., "Complete structure of lipid A obtained from the lipopolysaccharids of the heptoseless mutant of *salmonella* typhimurium." J. Biol. Chem.; 1983; pp. 12801-12803; vol. 258.
Verheuf, et al., "Beneficial effects of additional adjuvants on the immune response to haptenated liposomes." J. of Liposome Research; 1996; pp. 397-414; vol. 6(2).

\* cited by examiner

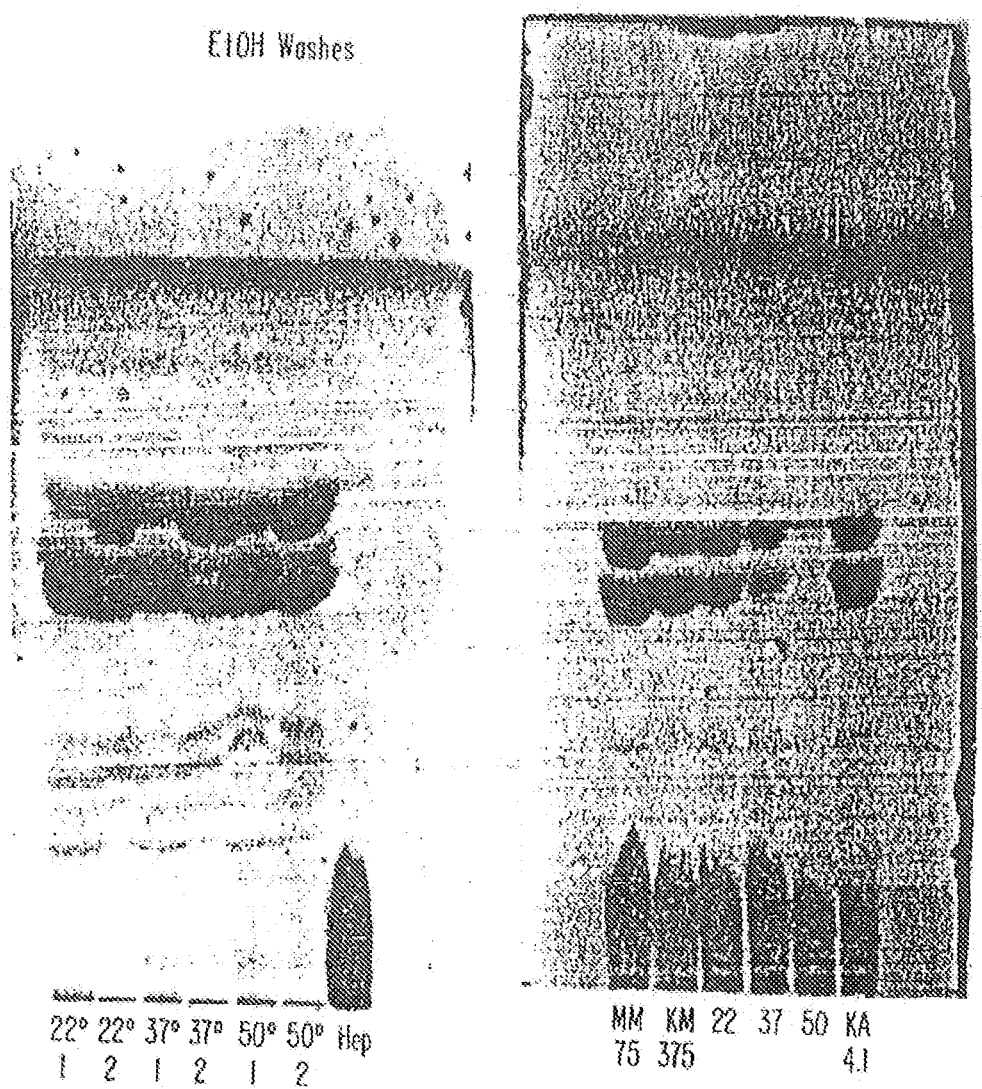

METHODS FOR THE PRODUCTION OF 3-O-DEACTIVATED-4'-MONOPHOSPHORYL LIPID A (3D-MLA)

This application is a continuation of U.S. application Ser. No. 11/621,306 filed Jan. 9, 2007, now abandoned, which is a continuation of U.S. application Ser. No. 10/099,313 filed Mar. 14, 2002, now abandoned, which claims priority to U.S. Provisional Application No. 60/280,089 filed Mar. 30, 2001.

STATEMENT AS TO RIGHTS TO INVENTIONS MADE UNDER FEDERALLY SPONSORED RESEARCH AND DEVELOPMENT

Not Applicable

BACKGROUND OF THE INVENTION

1. Field of the Invention

The present invention relates generally to the field of biosynthetic production of 3-O-deacylated-4'-monophosphoryl lipid A (3D-MLA). More particularly, it concerns methods of improving the yield of desired 3D-MLA congeners or minimizing the cost of purifying lipopolysaccharide (LPS) precursors of 3D-MLA.

2. Description of Related Art

It has long been recognized that enterobacterial lipopolysaccharides (LPS) are potent stimulators of the immune system. A variety of responses, both beneficial and harmful, can be elicited by submicrogram amounts of LPS. The fact that some of the responses are harmful, and some of these can be fatal, has precluded clinical use of LPS per se. It has been observed that the component of LPS most responsible for endotoxic activity is lipid A.

Accordingly, much effort has been made towards attenuating the toxic attributes of LPS or lipid A without diminishing the immunostimulatory benefits of these compounds. Notable among these efforts were those of Edgar Ribi and his associates, which resulted in the production of the lipid A derivative 3-O-deacylated-4'-monophosphoryl lipid A (3D-MLA; compositions comprising 3D-MLA are commercially available under the trade name MPL® from Corixa Corporation (Seattle, Wash.)). 3D-MLA has been shown to have essentially the same immunostimulatory properties as lipid A but lower endotoxicity (Myers et al, U.S. Pat. No. 4,912,094). Myers et al. also reported a method for production of 3D-MLA, as follows. First, LPS or lipid A obtained from a deep rough mutant strain of a gram-negative bacterium (e.g. *Salmonella minnesota* R595) is refluxed in mineral acid solutions of moderate strength (e.g. 0.1 N HCl) for a period of approximately 30 min. This leads to dephosphorylation at position 1 of the reducing-end glucosamine and decarbohydration at the 6' position at the non-reaming glucosamine of lipid A. Second, the dephosphorylated decarbohydrated lipid A (a.k.a. monophosphoryl lipid A or MLA) is subject to base hydrolysis by, for example, dissolving in an organic solvent such as chloroform:methanol (CM) 2:1 (v/v), saturating the solution an aqueous solution of 0.5 M $Na_2CO_3$ in pH 10.5, and flash evaporating solvent. This leads to selective removal of the β-hydroxymyristic acid moiety at position 3 of the lipid A, resulting in 3-O-deacylated-4'-monophosphoryl lipid A (3D-MLA).

The quality of the 3D-MLA produced by the above method is highly dependent on the purity and composition of the LPS obtained from the grain-negative bacterium. For one example, the lipid A component of LPS is a mixture of closely related species that contain between about 5-7 fatty acid moieties. In the formation of 3D-MLA, as is clear from the above discussion, one fatty acid moiety is removed, yielding 3D-MLA with between about 4-6 fatty acid moieties. It is generally held that 3D-MLA with at least 6 fatty acid moieties is preferred in terms of the combination of maintained or enhanced immunostimulatory benefits, reduced toxicity, and other desirable properties (Qureshi and Takayama, in "The Bacteria," Vol. XI (Iglewski and Clark, eds.), Academic Press, 1990, pp. 319-338).

For another example, commercial scale extraction of LPS from gram-negative bacteria typically involves the Chen method (Chen et al. *J. Infect. Dis.* 128:543 (1973)); namely, extraction with CM, which leads to an LPS- and phospholipid-rich CM phase from which LPS can later be purified. However, purification of LPS from the LPS- and phospholipid-rich CM phase typically requires multiple precipitation steps to obtain LPS of sufficient purity for use in immunostimulatory applications such as, for example, use as a vaccine adjuvant.

Therefore, it would be desirable to have methods for conveniently preparing highly pure LPS compositions. Further, it would be desirable to have methods for generating LPS compositions which compositions have 3D-MLA with increased levels of hexaacyl congeners.

Known fermentation techniques have been used to prepare cultures of gram-negative bacteria comprising readily purifiable LPS. These known techniques typically involve harvesting or bacterial cultures at early stationary phase, in keeping with standard bacteriological practices. However, it has been observed that the degree of acylation of LPS produced according to known conditions is variable. For example, the content of heptaacyl species in the lipid A of *S. minnesota* R595 can vary from 20% to 80%, depending on the batch (Rietschel et al., Rev. Infect. Dis. 9:S527 (19871). This variability in heptaracyl congener content would result in the significant differences in the hexaacyl congener content in the 3D MLA prepared from these LPS batches.

SUMMARY OF THE INVENTION

In one embodiment, the present invention relates to a method for producing lipopolysaccharide (LPS), comprising:
(a) growing a culture of a deep rough mutant bacterial strain in a medium;
(b) maintaining the culture in stationary phase for at least about 2 hr;
(c) harvesting cells from the culture; and
(d) extracting LPS from the cells.

The method allows for the production of an LPS that yields 3D-MLA with a relatively high proportion (i.e. at least about 20 mol %) of congeners comprising 6 fatty acid moieties.

In another embodiment, the present invention relates to a method of extracting lipopolysaccharide (LPS) from a culture of deep rough mutant bacterial strain cells, comprising:
(a) extracting the cells with a solution consisting essentially of at least about: 75 wt % of an aliphatic alcohol having from 1 to 4 carbon atoms and the balance water, thereby producing cells with reduced phospholipid content;
(b) extracting the cells with reduced phospholipid content with a solution comprising chloroform and methanol (CM), thereby yielding a solution of LPS in CM.

This method provides LPS solutions in CM that have reduced phospholipid content and that are therefore wellsuited to further modification and purification to 3D-MLA. The method involves relatively simple and inexpensive steps.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows TLC plates of ethanol extracts and LPS samples obtained with different temperatures during the ethanol extractions. The plate on the left shows, going from left to tight, the ethanol extracts at temperatures of 22° C., 37° C., and 50° C. The sample at the far right of this plate is an authentic LPS sample. The plate on the right shows the LPS obtained from each preparation. The samples in lanes 3, 4, and 5 correspond to LPS from cells subjected to pre-extractions with ethanol at 22° C. 37° C., and 50° C., respectively. The heavy bands at $R_f \sim 0.6$ correspond to phospholipid and fatty add impurities. The levels of these impurities are reduced by increasing the temperature of the ethanol extractions, and are very low in the sample that was pre-extracted at 50° C.

DESCRIPTION OF ILLUSTRATIVE EMBODIMENTS

In one embodiment, the present invention relates to a method for producing lipopolysaccharide (LPS), comprising:

(a) growing a culture of a deep rough mutant bacterial strain in a medium;
(b) maintaining the culture in stationary phase for at least about 2 hr;
(c) harvesting cells from the culture; and
(d) extracting LPS from the cells.

Lipopolysaccharides are the main lipid constituent in the outer leaflet of the outer membrane of gram-negative bacteria. The lipopolysaccharide fraction of a gram-negative bacterium comprises, among other components, lipid A. As has been described, lipid A can be decarbohydrated and partially dephosphorylated to yield monophosphoryl lipid A (MLA), and MLA can be selectively deacylated at position 3 to yield 3-O-deacylated-4'-monophosphoryl lipid A (3D-MLA).

However, lipid A produced by gram-negative bacteria typically comprises a number of species that have the same overall lipid A structure but differ in the number of fatty acid moieties they contain. Groups of lipid A species with the same number of fatty acids are referred to herein as "congeners." Lipid A congeners having from 4 to 7 fatty acid moieties are produced by standard commercial-scale culturing of gram-negative bacteria such as *S. minnesota* R595. As a result, the 3D-MLA produced from, e.g., *S. minnesota* R595 lipid A has a congener composition typically ranging from 3 to 6 fatty acid moieties (because 3D-MLA has undergone loss of one fatty acid moiety).

Heterogeneity in 3D-MLA (via lipid A and MLA) congener composition is attributable to two sources: (1) biosynthetic variability in the assembly of the lipid A and (2) loss of fatty acid moieties from the lipid A backbone during processing to 3O-MLA. Though not to be bound by theory, biosynthetic variability is believed to occur because of non-absolute substrate specificity of the acyltransferases involved in the terminal steps of lipid A biosynthesis, among other explanations. Loss of fatty acid moieties from the lipid A backbone may also occur during the acid and alkaline hydrolyses typically used in 3D-MLA production.

Surprisingly, it was discovered that 3D-MLA congener composition can be altered by altering the parameters of a process of culturing a deep rough mutant bacterial strain that produces lipid A. Specifically, it was discovered that maintaining the culture of the deep rough mutant bacterial strain at stationary phase for at least about 5 hr prior to harvesting results in a change in the proportions of lipid A congeners so produced such that, typically, at least about 20 mol % of the 30D-MLA later produced from the lipid A contains 6 fatty acids. Preferably, at least about 50 mol % of the 30-MLA contains 6 fatty acids. A maintenance at stationary phase time of about 5.5 hr has been found to be particularly effective. This is in distinction to the typical culturing processes known in the art, wherein harvesting occurs almost immediately after entry of the culture into the stationary phase; in the known process, the congener content of the LPS is highly variable and results in 3D-MLA with variable hexaacyl congener content.

By "deep rough mutant bacterial strain" is meant a strain of a gram-negative bacterium having a deep rough phenotype. A "deep rough" phenotype means that the polysaccharide moiety attached to the lipid A consists of only about 2-3 residues of 2-keto-3-deoxy-D-mannooctulonic acid (KDO). Preferably, the deep rough mutant bacterial strain is selected from the genus *Salmonella*. More preferably, if the deep rough mutant bacterial strain is of genus *Salmonella*, it is of species *Salmonella minnesota*, and even more preferably, it is strain *Salmonella minnesota* R595. Other deep rough mutant bacterial strains, such as *Proteus mirabilis* strains, among others, can be used.

Any technique appropriate for growing a deep rough mutant bacterial strain can be used. Typically, this will involve the use of at least one commercial-scale bioreactor. In one embodiment, the technique involves inoculating a relatively smell (e.g. 15 L) bioreactor with cells of the deep rough mutant bacterial strain, growing the deep rough mutant bacterial strain until a stationary phase, followed by aseptic transfer of the 15-L cell broth to a large (e.g. 750 L) bioreactor.

The growing can be performed on any medium known or discovered to allow the growth of the deep rough mutant bacterial strain. In one preferred embodiment, the medium is M9, a mixture of inorganic salts supplemented with dextrose and casamino acids. The composition of M9 is well-known to one of ordinary skill in the art.

After the deep rough mutant bacterial strain has been maintained at stationary phase for at least about 5 hr, the cells can be harvested from the culture and LPS extracted from the cells. Known techniques may be employed to harvest cells from the culture and extract LPS from the cells, although a preferred technique for extracting LPS from the cells is described below.

Harvesting can be performed by any known technique, in one preferred embodiment, after the cell culture has been maintained at stationary phase for at least about 5 hr, the contents of the bioreactor are pumped to a tangential filtration apparatus to separate spent medium from the cells.

The LPS is then extracted from the cells by any appropriate technique. Known techniques include the Galanos method, which involves extracting LPS with a mixture of phenol, chloroform, and petroleum ether (PCP), followed by evaporation of the chloroform and petroleum ether, addition of acetone and water to precipitate LPS, and recovery of LPS by centrifugation or filtration (Galanos et al., *Eur. J. Biochem*, 9:245 (1969)), and the Chen method, cited above, which involves extracting LPS with a mixture of chloroform and methanol (CM), followed by a series of methanol precipitation steps.

An improvement of the Chen method is described below, and is preferred for manufacture of LPS and its derivatives for commercial applications.

Regardless of the extraction technique, the result is a substantially pure dried LPS, which can be further processed by sequential add hydrolysis and base hydrolysis to form 3D-MLA, as is taught by Ribi, U.S. Pat. No. 4,436,727, and Myers et al., U.S. Pat. No. 4,912,094, which are hereby incorporated herein by reference. To summarize the teachings of these references as a preferred embodiment for the formation of 3D-MLA, the LPS is reacted with an organic or inorganic acid, and then lyophilized to produce MLA. The inorganic acid is preferably hydrochloric acid, sulfuric acid, or phosphoric, acid. The organic acid is preferably toluene sulfonic acid or trichloroacetic acid. The reaction may be performed at a temperature between about 90° C. and about 130° C. for a sufficient time to complete hydrolysis, commonly between about 15 min and about 60 min. The MLA may be treated with a solvent, preferably acetone, to dissolve fatty acids and other impurities, and the impurity-rich fatty acid solvent is removed.

Thereafter, the MLA is subjected to mild alkaline treatment to selectively remove the β-hydroxymyristic acid from position 3 of the MLA (under mild alkaline conditions, only the β-hydroxymyristic acid at position 3 is labile). The mild alkaline treatment can be carried out in aqueous or organic media. Appropriate organic solvents include methanol or other alcohols, dimethyl sulfoxide (DMSO), dimethylformamide (DMF), chloroform, dichloromethane, or mixtures thereof, among others. Combinations of water and organic solvents miscible with water may also be employed.

The alkaline base used to perform the hydroloysis is preferably selected from hydroxides, carbonates, phosphates, or amities. Illustrative inorganic bases include sodium hydroxide, potassium hydroxide, sodium carbonate, potassium bicarbonate, sodium bicarbonate, and potassium bicarbonate, among others. Illustrative organic bases include alkyl amines (such as diethylamine and triethylamine, among others), among others, In aqueous media, the pH is typically between about 10 and about 14, preferably between about 10 and about 12. The hydrolysis reaction is typically performed hum about 20° C. to about 80° C., preferably from about 50° C. to about 60° C. for a period of about 10 min to about 48 hr.

One preferred technique for alkaline hydrolysis involves dissolving MLA in CM 2:1 (v/v), saturating the solution with an aqueous buffer of 0.5 M at pH 10.5, and then flash evaporating the solvent at 45-50° C. under a vacuum aspirator (approximately 100 mm Hg).

In another embodiment, the present invention relates to a method of extracting lipopolysaccharide (LPS) from a culture of deep rough mutant bacterial strain cells, comprising:

(a) extracting the cells with a solution consisting essentially of at least about 75 wt % of an aliphatic alcohol having from 1 to 4 carbon atoms and the balance water, thereby producing culls with reduced phospholipid content;

(b) extracting the cells with reduced phospholipid content with a solution comprising chloroform and methanol, thereby yielding a solution of LPS in chloroform and methanol.

The deep rough mutant bacterial strain cells, the culture thereof, and methods of preparing the culture are as described above. Preferably, the deep rough mutant bacterial strain is selected from the genera *Salmonella* or *Escherichia*. More preferably, if the deep rough mutant bacterial strain is of genus *Salmonella*, it is of species *Salmonella minnesota*, and even more preferably, it is strain *Salmonella minnesota* R595. If the deep rough mutant bacterial strain is of genus *Escherichia*, more preferably it is of species *Escherichia coil*, and more preferably it is strain *Escherichia coli* D31m4.

The first extracting step can be performed with any short chain aliphatic alcohol. The aliphatic alcohol can be linear, branched, or cyclic. Preferably, the aliphatic alcohol has from 2 to 4 carbon atoms and is miscible with water. More preferably, the aliphatic alcohol is ethanol.

The solution comprising the aliphatic alcohol can comprise any proportion of aliphatic alcohol of 75 wt % greater. Preferably, the solution comprises between about 85 wt % and about 95 wt % aliphatic alcohol. Essentially the balance of the solution is water. Traces of other compounds may be present as a result of incomplete purification or other contamination of the aliphatic alcohol and water components of the solution.

The temperature at which the first extracting step is performed can be any temperature which is effective in providing sufficient extraction of phospholipid from the cultured cells. Preferably, the temperature is between about 35° C. and about 65° C. More preferably, the temperature is between about 45° C. and about 55° C.

Other parameters of the first extracting step, such as rate of addition of the aliphatic alcohol solution, duration of contact of the solution and the cells, and agitation or lack thereof, among others, can be routinely varied by one of ordinary skill in the art.

The first extracting step results in (i) a phospholipid-rich aliphatic alcohol solution phase and (ii) cells with a reduced phospholipid content. The LPS component of the cell membranes segregates substantially completely with the cells with a reduced phospholipid content.

The second extracting step involves extracting the cells with a reduced phospholipid content with a solution of chloroform:methanol (CM).

Any proportion of chloroform and methanol known to be suitable for use in extracting LPS from cell membranes (such as in the Chen method) may be used in the second extracting step. Typically, the proportion of chloroform to methanol is from about 2:1 to about 9:1. Solvent mixtures with properties equivalent to those of CM may also be used to obtain LPS from the cells with a reduced phospholipid content.

An advantage of the present method over the Chen method lies in the removal of phospholipid the first extracting step. Whereas the CM extraction of the Chen method results in an LPS solution that contains substantial levels of phospholipids, the second extracting step of the present invention, being performed on cells with a reduced phospholipid content, results in an LPS-rich solution that is substantially devoid of phospholipid. Alternative methods of producing LPS preparations that are relatively free of phospholipids, such as the method of Galanos (see above), are less desirable because they are not amenable to large scale production, they use solvent mixtures that pose health and safety concerns (e.g. phenol:chloroform:petroleum ether), or both.

Given the substantial absence of phospholipid from the LPS solution, further purification of the LPS according to this method is generally simpler and less expensive than under the Chen method. It has been found that a dry LPS residue of sufficient purity can be formed by evaporating the chloroform and methanol from the LPS solution.

Optionally, the LPS can be further processed, such by the acid hydrolysis and base hydrolysis steps described above, to produce MLA or 3D-MLA.

The 3D-MLA produced by following the methods described above can be used for a variety of purposes. One preferred use is as an immunostimulant or adjuvant for pharmaceutical compositions comprising an immunogenic polynucleotide, polypeptide, antibody, T-cell, or antigen-presenting cell (APC). The immunostimulant or adjuvant refers to essentially any substance that enhances or potentiates an immune response (antibody and/or cell-mediated) to an exogenous antigen.

One immune response which the MLA or 3D-MLA produced according to the present invention may stimulate is the Th1 type. A combination of monophosphoryl lipid A (MLA), preferably 3-de-O-acylated monophosphoryl lipid A (3D-MLA), together with an aluminum salt has been observed to be effective as an adjuvant for eliciting a predominantly Th1-type response. High levels of Th1-type cytokines (e.g., IFN-γ, TNFα, IL-2 and IL-12) lend to favor the induction of cell-mediated immune responses to an administered antigen. In contrast, high levels of Th2-type cytokines (e.g., IL-4, IL-5, IL-6 and IL-10) tend to favor the induction of humoral immune responses. Following application of a pharmaceutical composition comprising MLA or 3D-MLA, a patient will support an immune response that includes Th1- and Th2-type responses. When the response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145-173, 1989.

In one preferred embodiment, the adjuvant system includes the combination of monophosohoryl lipid A (MLA), preferably 3D-MLA, with a saponin derivative (such as Quil A or derivatives thereof, including QS21 and QS7 (Aquila Biopharmaceuticals Inc., Framingham, Mass.); Escin; Digitonin; or *Gypsophila* or *Chenopodium quinoa* saponins), such as the combination of QS21 and 3D-MLA adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MLA, and tocopherol in an oil-in-water emulsion is described in WO 95/17210.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

General Methods

A. Media Preparation

Cell growth was conducted in M9 medium, which is prepared by combining sterile solutions of inorganic salts, casamino acids, and dextrose. The M9 slat solution is typically prepared in the fermentor and contains the following salts: 2.0 g/L NaCl, 0.2 g/L MgSO$_4$.7H$_2$O, 3.0 g/L KH$_2$PO$_4$, 6.0 g/L Na$_2$HPO$_4$, and 1.0 g/L NH$_4$Cl. Sterile solutions of 20% (w/v) casamino acids (20 mL/L) and 50% (w/v) dextrose (32 mL/L) are then added aseptically to the fermentor to yield the completed medium.

B. Seed Growth

Typically, a sterile 250 mL Erlenmeyer flask was charged with 50 mL sterile M9 medium. A seed vial of *Salmonella minnesota* R595 (ca. $10^8$ cfu) was thawed and added to the flask, which was then stoppered with a gauze plug. The culture was incubated at 37° C. for 6-8 h, until robust growth is evident.

C. Cell Growth

Cultures of *Salmonella minnesota* R595 were grown in a BioFlo III fermentor (New Brunswick Scientific, Inc.) equipped with a 2.5 L glass vessel. In a typical run, the vessel was charged with 2.0 L of M9 salts solution, autoclaved, and sterile solutions of casamino acids and dextrose were then added aseptically. The fermentor was equipped with feedlines for antifoam (0.1% SAG-471, Witco Corp.) and NH$_4$OH (30%) as well as probes for pH, dO$_2$, and foam. The medium was adjusted to pH 6.9 using the NH$_4$OH feed. The fermentor was then inoculated with the entire seed culture and was incubated at 37° C. with air sparging (typically 2.0 Lpm) and stirring (typically 50 rpm). The growth phase of the culture was monitored by measuring optical density at 590 nm. Cells were harvested by either centrifugation or tangential flow filtration, washed with water, and lyophilized.

D. Extraction of Lipopolysaccharide (LPS)

LPS was isolated according to the procedure of Qureshi et at (1986) with minor modifications. In a typical run, the dried cells were first stirred at a concentration of 20 mg/mL in 90% ethanol (v/v) at room temperature for 1 h and were then recovered by vacuum filtration. The cells were subjected to a second ethanol extraction followed by sequential extractions with acetone and diethyl ether (15 min each, both at 40 mg/mL based on initial weight), and the resulting ether powder was allowed to air dry overnight. Meanwhile, a solution of phenol (89%):chloroform:petroleum ether 19:45:72 (v/v/v; abbreviated PCP) was prepared and allowed to stand overnight. The ether powder was suspended in PCP, which was decanted off of the excess water, at a concentration of 70 mg/mL. The solution was stirred for 30 min and then was centrifuged (3000×g, 15 min, 0-5° C.). The supernatant fraction was decanted into a round bottom flask and the cell pellet was extracted a second time with PCP. The supernatant fractions were combined and rotary evaporated at 40° C. until all volatile solvents were largely removed. The remaining volume was then measured. Water was added dropwise until a persistent turbidity was evident, and then 5 volumes acetone followed by 1 volume diethyl ether (both chilled in an ice bath) were added to the phenol solution with rapid mixing. The solution was placed in an ice bath for 30 min and then the precipitated LPS was recovered by centrifugation (5000×g, 15 min, 0.5° C.). It was generally necessary to gravity filter the supernatant fraction to recover any LPS that did not remain in the pellet. The LPS was washed one time in a minimal volume of cold acetone, recovered by centrifugation/filtration, and was then dried under vacuum. Typical yields were 4-5% based on the initial dry weight of cells.

E. Preparation of 4'-monophosphoryl lipid A (MLA)

LPS was suspended in water at a concentration of 10 mg/mL, using bath sonication at 45-55° C. to aid in dispersing the solid material. The resulting solution should be slightly turbid with no solid visible to the unaided aye. To this solution was added 1 volume of 0.2 N HCl, and it was then placed in a boiling water bath for 15 min. The reaction was quenched in an ice bath, and then was extracted with 5 volumes (relative to the initial LPS solution) of chloroform:methanol 2:1 (v/v). The biphasic solution was vortexed and the phases were separated by low speed centrifugation (500-1000×g). The lower phase was recovered and evaporated under nitrogen, yielding crude MLA.

F. Preparation of 3-O-deacylated-4'-monophosphoryl lipid A (3D-MLA)

Crude MLA was dissolved in chloroform:methanol 2:1 (v/v) at a concentration of between about 1-5 mg/mL, and 3.0 mL of this solution was transferred to a 16×100 mm test tube. An additional 0.4 mL of methanol was added to the tube, and it was then placed in a water bath at 50° C. for 10 min. The reaction was initiated by addition of 40 μL 0.5 M $KHCO_3$, pH 10.5, and the solution was incubated at 50° C. for 20 min. At the end of this time, the tube was removed from the water bath and the reaction was quenched by addition of 2.0 mL 0.1 N HCl (chilled) followed by vortexing. 3D-MLA was recovered by addition of 1.0 mL methanol, vortexing, centrifugation (500-1000×g), and evaporation of the lower (organic) phase to dryness under nitrogen.

EXAMPLE 2

Analytical Methods

A. Thin Layer Chromatography (TLC) of MLA and Related Samples

All TLC analyses were carried out using 5×10 cm plates coated with Silica Gel 60 (E Merck). Samples were generally applied to the TLC plates as 10 mg/mL solutions in chloroform:methanol 4:1 (v/v), with 3 μL solution (30 μg sample) applied in small spots to a 5 mm line using a capillary pipette. Plates were developed with a solvent system comprising chloroform/methanol/water/ammonium hydroxide 50:31:6:2 (v/v). Bands on the developed plates were visualized by spraying with a solution of 10% (w/v) phosphomolybdic acid in ethanol followed by charring at 150-160° C. In some cases, relative intensities of spots were quantified by scanning densitometry with a Shimadzu CS9000U Dual Wavelength Flying Spot Scanner (Shimadzu Corp.), using a scanning wavelength of 520 mn.

B. Analysis of MLA/3D-MLA by High Performance Liquid Chromatography (HPLC)

Samples to be analyzed were first converted to the free acid form by washing a solution of 3-5 mg sample in 5 ml chloroform:methanol (2:1 v:v) with 2 ml 0.1 N HCl. The biphasic system was vortexed, centrifuged, and the lower (organic) phase was transferred to a test tube and evaporated under a stream of nitrogen. The residue was the methylated by treatment with diazomethane. Briefly, an ethereal solution of diazomethane was prepared by placing 60-100 mg 1-methyl-3-nitro-1-nitrososguanidine (MNNG; Aldrich) in a 2 dram vial, adding 60 μL diethyl ether per mg MNNG, then adding 9 μL 5 N NaOH per mg MNNG while stirring the solution at <−10° C. Following completion of the reaction, the lemon yellow ether phase was dried by transferring it to a second vial that contained several pellets of NaOH and swirling, all while at <−10° C. The acid-washed sample was dissolved in 1 ml chloroform:methanol 4:1 (v:v) placed in a bath at <−10° C., and diazomethane solution was added dropwise with stirring until a faint yellow tint persists. The solvent was then evaporated at ambient temperature under a stream of nitrogen and was further dried under vacuum for at least 30 min.

Chromatographic analyses were conducted on a $C_{18}$ reverse phase column (Nova-Pak, 4 μm particle size, 8 mm×10 cm [Waters]). Methylated samples were dissolved in chloroform:methanol 4:1 (v/v) at a concentration of 100 μg/mL and passed through a 0.45 μm PTFE syringe filter. An injection volume of 20-25 μL was typically used, followed by elution with a linear gradient of 20 to 80% isopropanol in acetonitrile over 60 min at a flow rate of 2 ml/min with monitoring at 210 nm.

C. Analysis of LPS Congener Content by HPLC

LPS tends to be a highly heterogeneous material due to variability in 1) the number of sugar residues in the O-antigen and core regions, 2) polar substitutions in the core region and on the phosphates in the lipid A, and 3) the number and location of fatty acids attached to the lipid A backbone. It is this latter source of variability that is of interest relative to the congener content of 3D-MLA (MPL®). Hydrolysis of LPS to MLA and 3D-MLA removes variability in the O-antigen and core regions, however it also introduces additional heterogeneity due to uncontrolled loss of O-linked fatty acids. This prevents the acylation pattern in the intact LPS from being accurately known. As a way around this, a method was developed wherein the phosphates and the core region are removed under mild conditions that do not result in loss of O-linked fatty acids. The resulting dephosphorylated lipid A (zero phosphoryl lipid A, or ZPL) can then be analyzed by HPLC, yielding an accurate reflection of the acylation pattern in the parent LPS.

The method was typically carried out as follows. Between 0.5-5.0 mg of LPS sample was hydrolyzed in 200 μL concentrated hydrofluoric acid for 3-4 h at 27° C. This reaction must be done in a tightly capped Teflon tube and in a well-ventilated fume hood. The HF was removed by evaporation under a stream of nitrogen at ambient temperature, and the hydrolysate was then dissolved in chloroform:methanol 4:1 (v/v) and transferred to a 16×100 mm glass test tube, and solvent was evaporated under a stream of nitrogen. The residue was suspended in 1.0 mL 0.1% triethylamine using bath sonication, 1.0 mL 40 mM NaOAc was added, and the tube was suspended in a boiling water bath for 30-45 min. The reaction was quenched by cooling in an ice bath and the ZPL was recovered by extraction with 5 mL chloroform:methanol 2:1 (v/v). The organic phase was transferred to a small screw cap vial and solvent was evaporated under nitrogen. The ZPL was derivatized by adding 200 μL of 10 mg/mL O-(3,5-dinitrobenzyl)hydroxylamine HCl (Regis Technologies, Inc.) in pyridine, tightly capping the vial, then incubating at 60° C. for 3 h. Pyridine was evaporated under nitrogen and the residue was further dried under vacuum for >30 min. The residue was then suspended 500 μL chloroform:methanol (v/v) and loaded onto a 0.5-1.0 mL bed of Accell-QMA (acetate form; Waters) that had been pre-equilibrated in the same solvent. The column was rinsed with a total of 5.0 mL chloroform:methanol 2:1 (v/v) in several small portions and the eluate was collected in a 16×100 mm test tube. 2.0 mL 0.1 N HCl was added to the eluate, the biphasic system was vortexed, centrifuged briefly at 500-1000×g, and the lower (organic) phase was transferred to a another test tube and evaporated under nitrogen. The residue was dissolved in 100-300 µL chloroform:methanol 4:1 (v/v) and filtered through a 0.45 µm PTFE syringe filter. The filter was rinsed twice with chloroform:methanol 4:1 (v/v) and the filtrate was evaporated under nitrogen. The filtrate was finally taken up in 50-150 µL chloroform:methanol 4:1 (v/v) and transferred to an autoinjector vial for HPLC analysis. HPLC conditions were as follows: $C_{18}$ reverse phase column (e.g., Waters), 10 µL injection volume, linear gradient of 20 to 80% isopropanol in acetonitrile over 60 min at a flow rate of 2 ml/min, monitor at 254 nm.

EXAMPLE 3

Comparison of Congener Composition of MLA/3D-MLA from Cultures Harvested at Different Times A series of fermentor runs was conducted with the following parameters: 2.0 L M9 medium (initial pH 6.84-6.87), 2 Lpm air flow, stirring at 50 rpm, 37° C., no pH control. Cultures were monitored by measuring optical density at 590 nm and were stopped when the desired growth stage was attained. Cells were processed and extracted as described above to yield LPS samples, which were then hydrolyzed to MLA and 3D-MLA and analyzed by HPLE (see Examples 1 and 2). Results are summarized in Table 1.

TABLE 1

Congener composition of MLA and 3D-MLA from cells harvested at different ages.

| | | | MLA | | 3D-MLA |
|---|---|---|---|---|---|
| Run | Description | Culture age at harvest | Time in stationary phase | 3-O-deacylated hexaacyl | heptaacyl | 3-O-deacylated hexaacyl |
| A | Late exponential | 6.75 h | N/A | 12.4% | 12.2% | 9.9% |
| B | Early stationary phase | 9.5 h | ~0.5 h | 9.2% | 6.8% | 9.2% |
| C | Late stationary phase | 15 h | ~6 h | 19.5% | 13.2% | 21.5% |

The data show that cultures of *S. minnesota* R595 alter the acylation pattern of their LPS during stationary phase, resulting in an increase in the overall content of 3-O-deacylated hexaacyl plus heptaacyl species in MLA derived from this LPS, and this in turn gives rise to increased content of 3-O-deacylated hexaacyl species in 3D-MLA prepared from this MLA.

EXAMPLE 4

Comparison of Congener Composition of LPS from Cultures Harvested at Different Times A series of fermentor runs was conducted with the following parameters: 2.0 L M9 medium (initial pH 6.84-6.87), 2 Lpm air flow, stirring at 225 rpm, 37° C., no pH control. The growth stage of the cultures was monitored by measuring optical density at 590 nm. Cells were processed and extracted as described in Example 1 to yield LPS samples. LPS samples were hydrolyzed to ZPL and analyzed by HPLC as described in Example 2. Results are summarized in Table 2.

TABLE 2

Congener composition of LPS from cells harvested at different ages.

| | | Culture | | Congener content | | |
|---|---|---|---|---|---|---|
| Run | Description | age at time of harvest | Time in stationary phase | 3-O-acyl hexa-acyl | 3-O-deacylated hexaacyl | heptaacyl |
| A | Early stationary phase | 9 h | ~0.5 h | 76% | 0% | 24% |
| B | Late stationary phase | 15 h | ~6 h | 48% | 17% | 19% |

No 3-O-deacylated hexaacyl component was detected in the LPS from the early stationary phase cells (run A). Thus, the only source of hexaacylated congeners in 3D-MLA prepared from this LPS would be the heptaacylated material (24%). In contrast, LPS from cells harvested at late stationary phase contained both heptaacyl and 3-O-deacylated hexaacyl species (19% and 17%, respectively). Both of these species would contribute to the hexaacyl content in 3D-MLA (MPL®) prepared from this LPS. It was unexpected to find that cells produce 3-O-deacylated hexaacyl LPS species under certain conditions.

EXAMPLE 5

Effect of Pre-Extraction Temperature on Purity of *S. minnesota* R595 LPS

Cells of *S. minnesota* R595 were grown in an 80 L fermentor (New Brunswick Scientific) using essentially the same conditions as outlined in Example 1. The cells were concentrated by tangential flow filtration but were not centrifuged, and the slurry contained 51.5 mg dry cell mass per mL. Three solutions were prepared in which 150 mL aliquots of the cell suspension were each combined with 600 mL ethanol. The ethanol solutions were stirred for 1 h at 22° C., 37° C., and 50° C. and were filtered. The cells were subjected to a second ethanol extraction under the same conditions except using 95% ethanol. The cells were recovered by suction filtration and were then extracted overnight in chloroform:methanol 4:1 (v/v) at 50° C. The solutions were filtered and the filtrates were rotary evaporated to dryness, yielding the LPS preparations. Samples of the first and second ethanol extraction filtrates obtained at each temperature as well as the LPS obtained from the pre-extracted cells were analyzed by thin layer chromatography according to the method in Example 2. Images of the TLC plates are shown FIG. 1.

FIG. 1 shows TLC plates of ethanol extracts and LPS samples obtained with different temperatures during the ethanol extractions. The plate on the left shows, going from left to right, the ethanol extracts at temperatures of 22° C., 37° C., and 50° C. The sample at the far right of this plate is an authentic LPS sample. The plate on the right shows the LPS obtained from each preparation. The samples in lanes 3, 4, and 5 correspond to LPS from cells subjected to pre-extractions with ethanol at 22° C., 37° C., and 50° C., respectively. The heavy bands at $R_f$~0.6 correspond to phospholipid and fatty acid impurities. The levels of these impurities are reduced by increasing the temperature of the ethanol extractions, and are very low in the sample that was pre-extracted at 50° C.

It is apparent from the TLC plates in FIG. 1 that pro-extraction with ethanol at elevated temperatures is effective at removing impurities that are otherwise co-extracted with chloroform:methanol 4:1 (v/v). Pre-extraction at 50° C. results in LPS that is largely free of these impurities.

EXAMPLE 6

Comparison of LPS Obtained by with and without Pre-Extraction with Ethanol

Three batches of cells of *S. minnesota* R595 were grown in a 750 L fermentor (B. Braun) using essentially the same conditions as outlined in Example 1. Cells were harvested by tangential flow filtration, and a sample of the cell suspension was obtained from each batch and lyophilized. The bulk of the cells were subjected to two pro-extractions with 90% ethanol at 50° C. for 1 h. Cells were recovered by tangential flow filtration between extractions. The cells were than extracted overnight with chloroform:methanol 4:1 (v/v) at reflux. The extract was recovered by tangential flow filtration and evaporated to dryness. The lyophilized cell samples were extracted overnight in refluxing chloroform:methanol 4:1 (v/v), and the solutions were filtered and the filtrates were evaporated to dryness. LPS samples obtained with and without ethanol pre-extraction were analyzed by TLC essentially as described in Example 2. TLC plates were scanned from about $R_f$=0.01 to 0.90, and the ratio of intensity in the LPS region ($R_f$=0.01 to 0.020) to total intensity was calculated for each sample. The results are given in Table 3.

TABLE 3

LPS purity from cells with and without pre-extraction with ethanol.

| | Percent of total intensity in LPS region[1] | |
|---|---|---|
| Run | Lot Number | without ethanol pre-extraction | with ethanol pre-extraction |
| A | 48020-B2698C | 7 | 86 |
| B | 48020-C0598A | 11 | 83 |
| C | 48020-C0598B | 14 | 88 |

Note:
[1]Percent of total intensity in LPS region = [(intensity in $R_f$ = 0.01 to 0.20)/(intensity in $R_f$ = 0.01 to 0.90)] × 100

The results in Table 3 demonstrate that the LPS obtained following pre-extraction of *S. minnesota* R595 cells with 90% ethanol at 50° C. is substantially purer than material from cells without pre-extraction.

All or the methods disclosed and claimed herein can be made and executed without undue experimentation in light of the present disclosure. While the compositions and methods of this invention have been described in terms of preferred embodiments, it will be apparent to those of skill in the art that variations may be applied to the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of extracting lipopolysaccharide (LPS) from a culture of deep rough mutant bacterial strain cells, comprising:
   a) Extracting the cells with a solution consisting essentially of at least 75 wt % of an aliphatic alcohol having from 1 to 4 carbon atoms and the balance water, thereby producing cells with reduced phospholipid content;
   b) Extracting the cells with reduced phospholipid content with a solution comprising chloroform and methanol, thereby yielding a solution of LPS in chloroform and methanol,
   wherein the extracting with aliphatic alcohol is performed at a temperature between 35° C. and 65° C.

2. The method of claim 1, wherein the deep rough mutant bacterial strain is of the genera *Salmonella* or *Escherichia*.

3. The method of claim 2, wherein the deep rough mutant bacterial strain of genus *Salmonella* is of species *Salmonella minnesota*.

4. The method of claim 3, wherein the deep rough mutant bacterial strain of species *Salmonella minnesota* is strain *Salmonella minnesota* R595.

5. The method of claim 2, wherein the deep rough mutant bacterial strain of genus *Escherichia* is of species *Escherichia coli*.

6. The method of claim 5, wherein the deep rough mutant bacterial strain of species *Escherichia coil* is of strain *Escherichia coil* D31m4.

7. The method of claim 1, wherein the aliphatic alcohol has from 2 to 4 carbon atoms.

8. The method of claim 7, wherein the aliphatic alcohol is ethanol.

9. The method of claim 1, wherein the solution comprising aliphatic alcohol comprises between 85 wt % and 95 wt % aliphatic alcohol.

10. The method of claim 1, wherein the temperature is between 45° C. and 55° C.

11. The method of claim 1, further composing evaporating the chloroform and methanol from the LPS solution, thereby yielding a dry LPS residue.

12. The method of claim 11, further comprising subjecting the dry LPS residue to sequential acid hydrolysis and base hydrolysis, to form 3D-MLA.

* * * * *